United States Patent
Zhang et al.

(10) Patent No.: US 12,077,516 B2
(45) Date of Patent: Sep. 3, 2024

(54) SYSTEM AND METHOD FOR PREPARING EPOXY CHLOROPROPANE

(71) Applicants: QUZHOU JUHUA POLYAMIDE FIBRE LLC., Zhejiang (CN); Beijing University of Chemical Technology, Beijing (CN); Juhua Group Co., Ltd., Hangzhou Zhejiang (CN)

(72) Inventors: Liangliang Zhang, Beijing (CN); Liyang Zhou, Hangzhou Zhejiang (CN); Guangwen Chu, Beijing (CN); Bibo Xia, Zhejiang (CN); Jianfeng Chen, Beijing (CN); Yutu Jiang, Zhejiang (CN); Jihong Tong, Hangzhou Zhejiang (CN); Baochang Sun, Beijing (CN); Wei Mao, Zhejiang (CN); Yanchun Zheng, Zhejiang (CN)

(73) Assignees: QUZHOU JUHUA POLYAMIDE FIBRE LLC., Quzhou (CN); JUHUA GROUP CO., LTD, Zhejiang (CN); BEIJING UNIVERSITY OF CHEMICAL TECHNOLOGY, Beijing (CN)

( * ) Notice: Subject to any disclaimer, the term of this patent is extended or adjusted under 35 U.S.C. 154(b) by 0 days.

(21) Appl. No.: 18/269,109

(22) PCT Filed: Dec. 24, 2021

(86) PCT No.: PCT/CN2021/141200
§ 371 (c)(1),
(2) Date: Jun. 22, 2023

(87) PCT Pub. No.: WO2022/135564
PCT Pub. Date: Jun. 30, 2022

(65) Prior Publication Data
US 2024/0076277 A1  Mar. 7, 2024

(30) Foreign Application Priority Data
Dec. 25, 2020  (CN) .......................... 202011564263.7

(51) Int. Cl.
*C07D 303/08*  (2006.01)

(52) U.S. Cl.
CPC .................................. *C07D 303/08* (2013.01)

(58) Field of Classification Search
CPC ....................................................... C07D 303/08
See application file for complete search history.

(56) References Cited

FOREIGN PATENT DOCUMENTS

| CN | 202063710 | | 12/2011 | |
| CN | 105218492 | | 1/2016 | |
| CN | 112625008 | | 4/2021 | |
| CN | 112625008 A | * | 4/2021 | ........... C07D 301/26 |
| WO | 2020263076 | | 12/2020 | |

OTHER PUBLICATIONS

PCT/CN2021/141200, Written Opinion of the International Searching Authority, dated Mar. 23, 2022 (Year: 2022).*
International Search Report filed in PCT/CN2021/141200 mailed Mar. 23, 2022.

* cited by examiner

*Primary Examiner* — Matthew P Coughlin
(74) *Attorney, Agent, or Firm* — RANKIN, HILL & CLARK LLP

(57) ABSTRACT

A system and method for preparing epoxy chloropropane is provided in that by coupling three stages of high gravity reactors, the product epoxy chloropropane and water vapor are distilled from a reaction system in form of an azeotrope by adopting a water vapor steam stripping method. Further, by combining the azeotrope with the multiples stages of high gravity reactors, the gas phase mass transfer and the liquid phase mass transfer of the azeotrope are improved aiming at the features of the azeotrope in the reaction system, thus making the overall conversion rate higher. In addition, by combining steam stripping and high gravity, dichloropropanol and alkali solution are rapidly mixed for mass transfer, and the product epoxy chloropropane is rapidly distilled from the reaction system in the form of the azeotrope, such that the reaction proceeds continuously towards the direction of producing epoxy chloropropane, thus significantly improving the conversion rate.

10 Claims, 1 Drawing Sheet

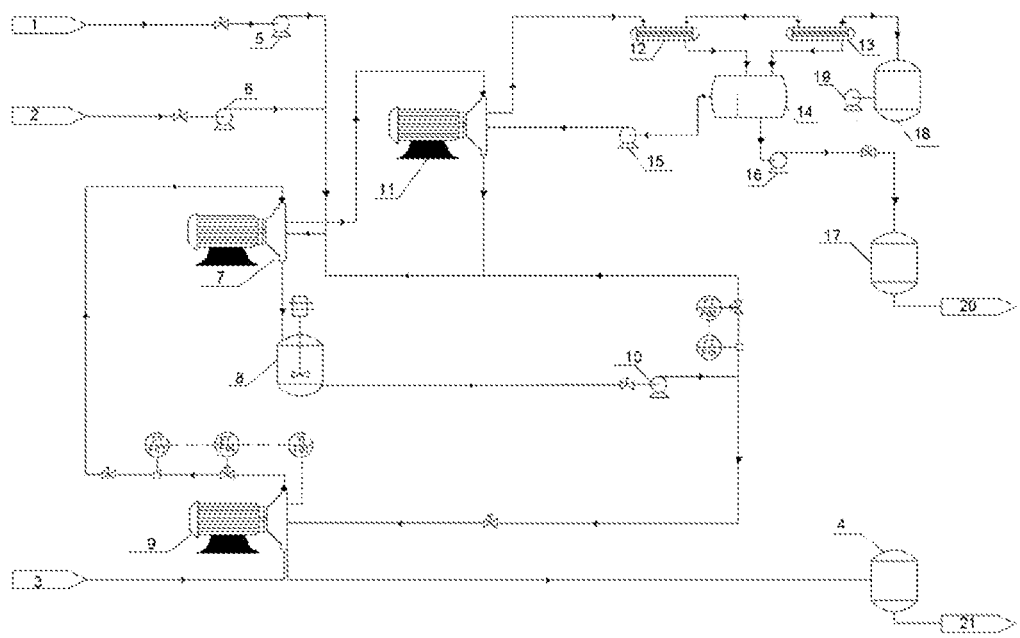

SYSTEM AND METHOD FOR PREPARING EPOXY CHLOROPROPANE

TECHNICAL FIELD

The present application relates to the field of preparing epoxy chloropropane, in particular to a system and method for preparing epoxy chloropropane.

BACKGROUND

Epoxy chloropropane (EPCH), also known as epichlorohydrin, is an important organic chemical raw material and fine chemical intermediate. It is mainly used for producing various products such as epoxy resin, nitroglycerin, explosives, glass fiber reinforced plastics and plasticizers, and has a broad market.

In industry, epoxy chloropropane is often produced by a propylene high-temperature chlorination method, a propylene acetate method and a glycerin method. Although the starting materials of the process technologies are different, they all involve a cyclization reaction step of synthesizing epoxy chloropropane from dichloropropanol and alkali solution. For the cyclization reaction of dichloropropanol to prepare epoxy chloropropane, the commonly used dichloropropanol is 1,3-dichloropropanol, and the commonly used alkali solution is sodium hydroxide, calcium hydroxide, etc. Considering the ultimate economic benefits, calcium hydroxide is generally selected as the alkali solution in industry.

At present, the mainstream production process for preparing epoxy chloropropane from calcium hydroxide and dichloropropanol in industry is the reaction of dichloropropanol and calcium hydroxide solution in a saponification tower. This process currently has many shortcomings, such as great likelihood of multiple side reactions and low product conversion rate.

SUMMARY

In order to solve at least one of the above problems, in one aspect, the present application provides a system for preparing epoxy chloropropane, including:
 a first high gravity reactor, a liquid inlet of the first high gravity reactor being communicated with a liquid inlet pipeline of raw materials dichloropropanol and alkali solution;
 a second high gravity reactor, a gas inlet of the second high gravity reactor being communicated with a water vapor pipeline, a gas outlet of the second high gravity reactor being communicated with a gas inlet of the first high gravity reactor;
 a liquid circulation tank, an inlet of the liquid circulation tank being communicated with a liquid outlet of the first high gravity reactor, an outlet of the liquid circulation tank being respectively communicated with the liquid inlet of the first high gravity reactor and a liquid inlet of the second high gravity reactor; and
 a third high gravity reactor, a gas inlet of the third high gravity being communicated with a gas outlet of the first high gravity reactor, a liquid outlet of the third high gravity being communicated with the liquid inlets of the first high gravity reactor and the second high gravity reactor, a gas outlet of the third high gravity reactor being communicated with a recovery device, a liquid inlet of the third high gravity reactor being communicated with a liquid outlet of the recovery device, wherein
 a liquid outlet of the second high gravity reactor is communicated with an inlet of a chloride salt solution storage tank.

In a preferred example, the system further includes:
 a first valve located on a pipeline between the outlet of the liquid circulation tank and the liquid inlet of the first high gravity reactor; and
 a second valve located on a pipeline between the outlet of the liquid circulation tank and the liquid inlet of the second high gravity reactor.

In a preferred example, the system further includes:
 a valve controller coupled with the first valve and/or the second valve and configured to control the opening of the corresponding valve.

In a preferred example, the system further includes:
 a detector configured to detect flow rate at the liquid inlet pipeline of raw materials dichloropropanol and alkali solution; and
 a processor configured to determine the opening of the corresponding valve according to the flow rate.

In a preferred example, the recovery device includes:
 a first condenser and a second condenser in series, a gas inlet of the first condenser being communicated with a gas outlet of the third high gravity reactor; and
 a two-phase separator communicated with liquid outlets of the first condenser and the second condenser, a liquid outlet of the two-phase separator being communicated with the liquid inlet of the third high gravity reactor.

In a preferred example, the second high gravity reactor and the third high gravity reactor are rotating packed beds, and the first high gravity reactor is a rotor-stator reactor.

In a preferred example, the two-phase separator includes a separation chamber and a baffle provided in the separation chamber, the baffle divides the separation chamber into two communicated sub-chambers, one sub-chamber is communicated with the third high gravity reactor, and the other sub-chamber is communicated with a storage tank.

In a preferred example, the baffle is movable.

In a preferred example, the second high gravity reactor and the third high gravity reactor are rotating packed beds, and an oleophobic packing is provided in the rotating packed beds.

The present application further provides a method for preparing epoxy chloropropane, including: preparing epoxy chloropropane by using the system.

The Present Application has the Following Beneficial Effects:

The present application provides a system and method for preparing epoxy chloropropane. In the present application, by coupling three stages of high gravity reactors, the product epoxy chloropropane and water vapor are distilled from a reaction system in form of an azeotrope by adopting a water vapor steam stripping method, and the product obtained using the method has high purity. On the one hand, water vapor is replenished through an external water vapor source, and on the other hand, it can be recycled from the second high gravity reactor and the third high gravity reactor to form a water vapor cycle, thus ensuring the amount of water vapor used and not requiring a large amount of water vapor. Further, the combination of the azeotrope with the multiple stages of high gravity reactors greatly improves the gas-phase and liquid-phase mass transfer effect of the azeotrope aiming at the features of the azeotrope in the reaction system of the present application, thus improving the overall conversion rate of the reaction. In addition, by combining steam stripping and high gravity, dichloropropanol and alkali solution are rapidly mixed for mass transfer, and the product epoxy chloropropane is rapidly distilled from the reaction system in form of the azeotrope (based on rapid diffusion of water vapor), such that the reaction proceeds continuously towards the direction of producing epoxy chloropropane, thus significantly improving the conversion rate. As proved by a test apparatus, the present application can make the conversion rate of dichloropropanol reach 99.6% or more and make the purity of the product epoxy chloropropane reach 99% or more.

DESCRIPTION OF THE DRAWINGS

In order to describe the technical solutions in the examples of the present application or the existing technologies more clearly, the drawings used in the description of the examples or existing technologies will be briefly introduced below. Obviously, the drawings in the following description are only some examples of the present application. Those skilled in the art may obtain other drawings according to these drawings without contributing any inventive labor.

FIG. 1 illustrates a schematic diagram of a system for preparing epoxy chloropropane according to an example of the present application.

Description of reference signs in FIG. 1: 1—dichloropropanol inlet; 2—alkali solution inlet; 3—water vapor inlet; 4—No. 1 storage tank; 5—No. 1 pump; 6—No. 2 pump; 7—first high gravity reactor; 8—circulation buffer kettle; 9—second high gravity reactor; 10—circulating pump; 11—third high gravity reactor; 12—first condenser; 13—second condenser; 14—two-phase separator; 15—No. 3 pump; 16—No. 4 pump; 17—No. 2 storage tank; 18—vacuum buffer tank; 19—vacuum pump; 20—epoxy chloropropane outlet; 21—chloride salt solution outlet.

DESCRIPTION OF THE EMBODIMENTS

The technical solutions in the examples of the present application will be clearly and completely described below with reference to the drawings in the examples of the present application. Obviously, the described examples are only a part of the examples of the present application, not all of them. All other examples obtained by those skilled in the art based on the examples of the present application without contributing any inventive labor still fall within the scope of protection of the present application.

As found by the inventor through research, at present, the mainstream production process for preparing epoxy chloropropane through reaction between calcium hydroxide and dichloropropanol involves the reaction of dichloropropanol and calcium hydroxide solution in a saponification tower. However, there are many shortcomings, such as low product conversion rate and great likelihood of multiple side reactions. There is still no good solution in the industry. At the same time, industry researchers are unaware of the reason for the shortcomings, and research progress in related areas has been stagnant.

As found by the inventor through experimental exploration, the reason for the shortcomings is poor fluidity since liquid flows on tower plates only by virtue of gravity when multiple baffle tower plates are provided in the saponification tower, resulting in insufficient contact between the oil and water phases. In addition, calcium hydroxide is very easy to stick and the pressure drop inside the tower is large, making it difficult to transfer products in time, resulting in low conversion rate. Moreover, due to the long contact time of oil and water phases in the saponification tower, it is easy for multiple side reactions to occur.

Details are as follows:

(1) There are many byproducts and the selectivity of epoxy chloropropane is poor. The reaction equation for the reaction of calcium hydroxide with dichloropropanol to produce epoxy chloropropane is as follow:

$$2C_3H_5Cl_2OH+Ca(OH)_2 \rightarrow 2CH_2OCHCH_2Cl+CaCl_2+H_2O \quad (1)$$

However, in the traditional saponification tower, the liquid can only flow laterally by gravity, and the oil phase and the water phase cannot fully contact, resulting in the high concentration of alkali at local positions. Excessive alkali is easy to cause the following nucleophilic substitution reactions with dichloropropanol to produce monochloropropanediol and glycerol:

$$2C_3H_5Cl_2OH+Ca(OH)_2 \rightarrow 2CH_2ClCHOHCH_2OH+CaCl_2 \quad (2)$$

$$C_3H_5Cl_2OH+Ca(OH)_2 \rightarrow CH_2OHCHOHCH_2OH+CaCl_2 \quad (3)$$

In the traditional saponification tower, the produced epoxy chloropropane cannot be separated from the reaction system in time, and it is easy to further cause reactions such as hydrolysis and nucleophilic substitution in the system to produce monochloropropanediol and glycidol:

$$CH_2OCHCH_2Cl+H_2O \rightarrow CH_2OHCHOHCH_2Cl \quad (4)$$

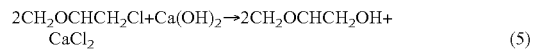

$$2CH_2OCHCH_2Cl+Ca(OH)_2 \rightarrow 2CH_2OCHCH_2OH+CaCl_2 \quad (5)$$

The comprehensive effect of the side reactions above leads to low purity of epoxy chloropropane produced by the existing processes and a large amount of reaction byproducts. According to the survey, the purity of epoxy chloropropane products obtained by mainstream processes is only about 95% (mass fraction).

(2) Calcium hydroxide easily blocks the reactor. Since calcium hydroxide is slightly soluble in water, in the traditional saponification tower, the degree of liquid turbulence is poor and calcium hydroxide easily blocks the tower plates, resulting in an increase in pressure drop inside the tower and high steam consumption. Frequent shutdown and pickling are required, which takes a long time and increases production costs.

(3) The concentration of calcium chloride in saponification solution is low. As described previously, since the saponification tower plates in existing processes are easily blocked by calcium hydroxide, calcium hydroxide solution with larger flow rate and lower concentration is often used in actual production. Moreover, due to the poor separation effect of the existing process and the high pressure drop of tower plates in the saponification tower, the steam consumption is high. The water vapor fed into the system is finally condensed and enters the saponification solution, resulting in a large amount of saponification solution containing low-concentration calcium chloride. Heat recovery treatment such as mother liquor distillation is required, which significantly increases energy consumption and the occupied area of the device. According to the survey, the current mainstream process uses 20% (mass fraction) calcium hydroxide as fresh alkali solution for the reaction, and the extracted concentration of calcium chloride is only about 10%.

(4) The conversion rate of dichloropropanol is low, and the residual organic matter in the saponification solution is high. Due to the poor mixing and mass transfer effect in the existing saponification tower, the reaction is incomplete, the raw material conversion rate is low, and many byproducts are produced. Moreover, due to the poor separation effect of the existing process, part of the product epoxy chloropropane is not carried out by water vapor, enters the saponification solution and is discharged. The above reasons lead to high content of organic substances such as dichloropropanol and epoxy chloropropane in the saponification solution waste of the existing process. Wastewater containing epoxides has a killing effect on microorganisms, making it difficult to treat them using biodegradation methods. Therefore, it is necessary to add wastewater treatment devices, which significantly increases the investment. According to the survey, the COD value in the saponification solution extracted by the current mainstream process is generally 10000 ppm or more.

(5) The consumption of steam is large. In the traditional saponification tower, water vapor enters from the bottom of the tower, one part of which is used for preventing calcium hydroxide from blocking the tower plates and the other part of which is used for distilling the product. Due to the structural design of the multi-layer baffle tower plates in the saponification tower and the poor mass transfer effect between the steam, oil phase, water phase and partially precipitated calcium hydroxide solids, the pressure drop n the saponification tower is large and the steam consumption is great. According to the survey, the existing process uses 74% (mass fraction) raw material dichloropropanol for reaction, and the steam consumption is 640 Kg/(t of epoxy chloropropane).

In view of this, the present application provides a novel preparation system. Referring to FIG. 1, the system specifically includes:

a first high gravity reactor 7, a liquid inlet of the first high gravity reactor 7 being communicated with a liquid inlet pipeline of raw materials dichloropropanol 1 and alkali solution 2;

a second high gravity reactor 9, a gas inlet of the second high gravity reactor 9 being communicated with a water vapor pipeline 3, a gas outlet of the second high gravity reactor 9 being communicated with a gas inlet of the first high gravity reactor 7;

a liquid circulation tank 8, an inlet of the liquid circulation tank 8 being communicated with a liquid outlet of the first high gravity reactor 7, an outlet of the liquid circulation tank 8 being respectively communicated with the liquid inlet of the first high gravity reactor 7 and a liquid inlet of the second high gravity reactor 9; and a third high gravity reactor 11, a gas inlet of the third high gravity 11 being communicated with a gas outlet of the first high gravity reactor 7, a liquid outlet of the third high gravity 11 being communicated with the liquid inlets of the first high gravity reactor 7 and the second high gravity reactor 9, a gas outlet of the third high gravity reactor 11 being communicated with a recovery device, a liquid inlet of the third high gravity reactor 11 being communicated with a liquid outlet of the recovery device, wherein a liquid outlet of the second high gravity reactor 9 is communicated with an inlet of a chloride salt solution storage tank.

In the present application, by coupling three stages of high gravity reactors, the product epoxy chloropropane and water vapor are distilled from a reaction system in form of an azeotrope by adopting a water vapor steam stripping method, and the product obtained using the method has high purity. On the one hand, water vapor is replenished through an external water vapor source, and on the other hand, it can be recycled from the second high gravity reactor and the third high gravity reactor to form a water vapor cycle, thus ensuring the amount of water vapor used and not requiring a large amount of water vapor. Further, the combination of the azeotrope with the multiple stages of high gravity reactors greatly improves the gas-phase and liquid-phase mass transfer effect of the azeotrope aiming at the features of the azeotrope in the reaction system of the present application, thus improving the overall conversion rate of the reaction. In addition, by combining steam stripping and high gravity, dichloropropanol and alkali solution are rapidly mixed for mass transfer, and the product epoxy chloropropane is rapidly distilled from the reaction system in form of the azeotrope (based on rapid diffusion of water vapor), such that the reaction proceeds continuously towards the direction of producing epoxy chloropropane, thus significantly improving the conversion rate. As proved by a test apparatus, the present application can make the conversion rate of dichloropropanol reach 99.6% or more and make the purity of the product epoxy chloropropane reach 99% or more.

It is to be understood that the present application innovatively adopts the steam stripping method and reuses the water vapor required by the system itself as steam for steam stripping. On the one hand, it does not increase the equipment cost and only requires pipeline reconstruction. On the other hand, the steam stripping method is adopted to quickly remove the product in azeotropic form, which can quickly transfer the product, such that the reaction proceeds continuously towards the direction of producing epoxy chloropropane, thus significantly improving the conversion rate.

In an example not illustrated in FIG. 1, the system further includes:

a first valve located on a pipeline between the outlet of the liquid circulation tank and the liquid inlet of the first high gravity reactor; and a second valve located on a pipeline between the outlet of the liquid circulation tank and the liquid inlet of the second high gravity reactor.

In this example, by controlling the first value and the second valve, the flow rate in the two high gravity reactors can be adjusted, thus achieving dynamic control. In addition, the first valve and the second valve substantively control the flow rate returned to the second high gravity reactor, thus controlling the reaction balance of the second high gravity reactor and improving the overall reaction conversion rate.

Further, in some examples, the system further includes:

a valve controller coupled with the first valve and/or the second valve and configured to control the opening of the corresponding valve.

In this example, the opening of the valve can be automatically controlled through the valve controller, thus not requiring manual control.

Further, the system further includes:

a detector configured to detect flow rate at the liquid inlet pipeline of raw materials dichloropropanol and alkali solution; and a processor configured to determine the opening of the corresponding valve according to the flow rate.

In this example, the flow rate of the raw material inlet can be detected by the detector, and the opening of the valve can be adjusted based on the flow rate feedback. That is, the adjustment in this example is based on overall flow rate control, is pertinent and can achieve automatic and dynamic adjustment.

In addition, in an example of the present application, the recovery device includes:
- a first condenser and a second condenser in series, a gas inlet of the first condenser being communicated with a gas outlet of the third high gravity reactor; and
- a two-phase separator communicated with liquid outlets of the first condenser and the second condenser, a liquid outlet of the two-phase separator being communicated with the liquid inlet of the third high gravity reactor.

In this example, by connecting the first condenser and the second condenser in series, and pumping part of the residual liquid into the third high gravity reactor through the two-phase separator, it is then recycled into the entire reaction cycle through cycle management.

In a preferred example, the two-phase separator includes a separation chamber and a baffle provided in the separation chamber, the baffle divides the separation chamber into two communicated sub-chambers, one sub-chamber is communicated with the third high gravity reactor 11, and the other sub-chamber is communicated with a storage tank 17.

In this example, two-phase separation is achieved by using the baffle, the operation is simple and the equipment cost is low.

Further, in order to achieve the dynamic balance adjustment of the entire reaction, the baffle is movable.

In addition, in the present application, the high gravity reactors may be pertinently selected, the second high gravity reactor and the third high gravity reactor are rotating packed beds, and the first high gravity reactor is a rotor-stator reactor.

In this example, for the steam stripping of water vapor, the dispersion and mixing of the gas phase are emphasized, and the packings in the rotating packed beds are used for mass transfer and mixing, thus greatly improving the overall dispersion effect and the steam stripping effect. The stator and rotor are used for liquid reaction, thus increasing the collision area of the liquid and improving the liquid-phase reaction efficiency.

Further, in order to avoid blockage, the second high gravity reactor and the third high gravity reactor are a rotating packed bed, and an oleophobic packing is provided in the rotating packed beds.

It is to be understood that high gravity technology is a typical process intensification technology that has been successfully applied in various industrial processes that intensify mass transfer, heat transfer and micro mixing, and has achieved excellent results. It has the characteristics of small equipment floor area, short residence time, high mass transfer efficiency, and high reaction speed and efficiency.

The present application combines the high gravity technology with the steam stripping technology and applies it to the preparation process of epoxy chloropropane. In the first high gravity reactor, the alkali solution and the raw material dichloropropanol are fully mixed and react quickly. At the same time, under the action of water vapor, the reaction system undergoes sufficient turbulence and efficient mass and heat transfer. The product epoxy chloropropane and water vapor are distilled from the reaction system in the form of an azeotrope. In the second high gravity reactor and the third high gravity reactor, the liquid and gas discharged from the first reactor are further purified, and the unreacted raw materials are recycled back to the first high gravity reactor. The high-purity product epoxy chloropropane and byproduct chloride salt are extracted respectively.

In the example of the present application, the system may be divided into units according to functions, specifically including a reaction unit, a chloride salt purification unit, and a product purification unit.

(1) Reaction unit: the raw materials dichloropropanol and alkali solution are continuously added to the first high gravity reactor according to a certain ratio and the feed liquid is crushed into small liquid droplets and liquid films, is fully mixed, and reacts quickly. At the same time, the water vapor passing through the second high gravity reactor is continuously fed into the first high gravity reactor, causing sufficient turbulence of the reaction feed liquid, and sufficient mass and heat transfer between the water vapor and the reaction feed liquid. The product epoxy chloropropane in the feed liquid in the first high gravity reactor is distilled together with water vapor in the form of an azeotrope, and then fed into the third high gravity reactor. The liquid after reaction in the first high gravity reactor (mainly chloride salt solution and a small amount of incompletely reacted alkali solution and dichloropropanol) is fed into the circulation buffer kettle. The liquid (mainly chloride salt solution and a small amount of incompletely reacted alkali solution and dichloropropanol) that is fed into the circulation buffer kettle from the first high gravity reactor is extracted by the circulating pump and divided into two streams. One stream is used as the circulating liquid to be fed into the first high gravity reactor for further reaction, and the other stream is fed into the second high gravity reactor.

(2) Chloride salt purification unit: the liquid (mainly chloride salt solution and a small amount of incompletely reacted alkali solution and dichloropropanol) fed into the second high gravity reactor is in full contact with water vapor in the second high gravity reactor for rapid heat and mass transfer. The organic matter entrained in the liquid is vaporized by water vapor and brought into the first high gravity reactor for further reaction. The remaining liquid is chloride salt solution with low organic matter content, which flows out of the second high gravity reactor and then flows to the chloride salt storage tank.

(3) Product purification unit: the azeotropic gas entering the third high gravity reactor from the first high gravity reactor fully contacts the reflux condensate in the third high gravity reactor, achieving rapid mass and heat transfer. The incompletely reacted dichloropropanol and other byproducts entrained in the gas are washed into the liquid phase and reflux into the first high gravity reactor for continuous reaction. A small amount of epoxy chloropropane contained in the reflux condensate is stripped into the gas phase through stream stripping and discharged from the top of the third high gravity reactor along with the azeotropic gas. The gas discharged from the top of the third high gravity reactor is completely condensed into liquid after passing through the two stages of condensers, and a small amount of non-condensable gas is discharged from the top of the second condenser. The top gas outlet of the second condenser is connected to the vacuum pump through the vacuum buffer tank. The liquid completely condensed through the two stages of condensers is fed into the two-phase separator, where the oil phase (product epoxy chloropropane) and water phase (steam condensate) are layered. The water phase is returned to the third high gravity reactor as the reflux condensate mentioned above. The oil phase is extracted from the epoxy chloropropane storage tank as a product.

Specifically, the high gravity field level in the first high gravity reactor is 50-1800 g, preferably 80-1200 g. The high gravity field level in the second high gravity reactor is 20-1200 g, preferably 50-800 g. The high gravity field level in the third high gravity reactor is 20-1200 g, preferably 50-800 g. The temperature of the reaction material in the first high gravity reactor is 50-90° C., preferably 60-85° C. The mass fraction of the raw material dichloropropanol is 20-98%. The alkali solution includes but is not limited to calcium hydroxide solution, sodium hydroxide solution, potassium hydroxide solution, ammonia or mixtures thereof. The feed alkali solution has a stoichiometric excess of 5-30% relative to dichloropropanol (ratio of converted pure substances). The mass flow rate ratio of the circulating liquid flowing into the first high gravity reactor for further reaction to the liquid flowing into the second high gravity reactor is 1-10, preferably 4-8. The amount of water vapor fed into the second high gravity reactor is 200-500 Kg/(t of epoxy chloropropane). The vacuum pump maintains a vacuum degree of 20-90 KPa throughout the entire system. The temperature of the water vapor and epoxy chloropropane azeotropic gas fed from the first high gravity reactor to the second high gravity reactor is 60-90° C., preferably 70-88° C., with water content of about 28%. The temperature of the reflux condensate is 4-13° C.

The preparation system according to the present application will be described below in detail with reference to FIG. 1. Referring to FIG. 1, the system specifically includes a dichloropropanol inlet (1), an alkali solution inlet (2), a water vapor inlet (3), a No. 1 storage tank (4), a No. 1 pump (5), a No. 2 pump (6), a first high gravity reactor (7), a circulation buffer kettle (8), a second high gravity reactor (9), a circulating pump (10), a third high gravity reactor (11), a first condenser (12), a second condenser (13), a two-phase separator (14), a third pump (15), a fourth pump (16), a No. 2 storage tank (17), a vacuum buffer tank (18), a vacuum pump (19), an epoxy chloropropane outlet (20), and a chloride salt solution outlet (21). The raw material dichloropropanol inlet (1) and the alkali solution inlet (2) are respectively connected with a liquid inlet of the first high gravity reactor (7) through the No. 1 pump (5) and the No. 2 pump (6). A liquid outlet of the first high gravity reactor (7) is connected with a liquid inlet of the circulation buffer kettle (8). A liquid outlet of the circulation buffer kettle (8) is connected with an inlet of the circulating pump (10). An outlet of the circulating pump (10) is connected with the liquid inlet of the first high gravity reactor (7). A bypass is provided between the outlet of the circulating pump (10) and the liquid inlet of the first high gravity reactor (7). The bypass connects the outlet of the circulating pump (10) to the liquid inlet of the second high gravity reactor (9). The water vapor inlet (3) is connected with a gas inlet of the second high gravity reactor (9). A gas outlet of the second high gravity reactor (9) is connected with a gas inlet of the first high gravity reactor (7). A liquid outlet of the second high gravity reactor (9) is connected with a liquid inlet of the first storage tank (4). A liquid outlet of the No. 1 storage tank (4) is connected with the chloride salt solution outlet (21). A gas outlet of the first high gravity reactor (7) is connected with a gas inlet of the third high gravity reactor (11). A liquid outlet of the third high gravity reactor (11) is connected with a liquid inlet of the first high gravity reactor (7). A gas outlet of the third high gravity reactor (11) is connected with an inlet of the first condenser (12). A gas outlet of the first condenser (12) is connected with an inlet of the second condenser (13). A liquid outlet of the first condenser (12) and a liquid outlet of the second condenser (13) are both connected with an inlet of the two-phase separator (14). A gas inlet of the second condenser (13) is connected with an inlet of the vacuum buffer tank (18). An outlet of the vacuum buffer tank (18) is connected with the vacuum pump (19). A water phase outlet of the two-phase separator (14) is connected with an inlet of the third pump (15). An outlet of the No. 3 pump (15) is connected with a liquid inlet of the third high gravity reactor (11). An oil phase outlet of the two-phase separator (14) is connected with an inlet of the No. pump (16). An outlet of the No. 4 pump (16) is connected with an inlet of the No. 2 storage tank (17). An outlet of the No. 2 storage tank (17) is connected with the epoxy chloropropane outlet (20).

It is to be understood that the present application has the following detailed effects due to the combination of high gravity equipment with water vapor steam stripping:

(1) The conversion rate of raw materials and the selectivity of products are improved. The occurrence of side reactions is inhibited. The content of byproducts is reduced. The purity of the product epoxy chloropropane is improved. The first high gravity reactor in the present application can enhance the complex mixing, mass transfer and heat transfer processes among the oil phase (dichloropropanol), the water phase (alkali solution), the steam and the partially precipitated solid alkali and salt by crushing liquid droplets, shearing the fluid, enhancing turbulence and other methods, thus achieving the rapid and uniform mixing of dichloropropanol and alkali solution, accelerating the main reaction rate and inhibiting the side reactions. At the same time, the water vapor is in full contact with the reaction liquid for rapid mass and heat transfer. The product epoxy chloropropane is quickly distilled from the reaction system in the form of an azeotrope, such that the reaction proceeds continuously towards the direction of producing epoxy chloropropane, thus significantly improving the conversion rate. As proved by a test apparatus, the present application can make the conversion rate of dichloropropanol reach 98% or more, and make the purity of the product epoxy chloropropane reach 97% or more.

(2) The problem of equipment blockage is effectively solved. Due to the strong centrifugal force field in the high gravity reactor, the turbulence of the liquid is relatively high, the oil and water phases are mixed quickly and uniformly, and the solid and liquid are fully dissolved, thus avoiding the problem of equipment blockage caused by precipitated alkali and salt, not requiring regular shutdown and prickling of equipment, achieving continuous production, and reducing production costs.

(3) The concentration of chloride salt in the extracted solution of chloride salt is significantly increased. As described above, in the present application, by coupling the reaction and separation processes through the three stages of high gravity reactors, the reaction and separation processes are performed efficiently, the steam consumption is greatly reduced, the amount of steam condensate is greatly reduced, and the concentration of chloride salt in the extracted solution of chloride salt is significantly increased, so that the extracted solution of calcium chloride does not require concentration and heat treatment, thus improving the production efficiency. The test apparatus using the present application uses calcium hydroxide with a mass fraction of 20%, and the extracted concentration of calcium chloride can reach 33%.

(4) The content of the organic matters in the extracted solution of chloride salt is significantly decreased. As described above, in the present application, by coupling the reaction and separation processes through the three stages of high gravity reactors, the reaction and separation processes are performed efficiently, the conversion rate of dichloropropanol and the purity of epichlorohydrin are significantly improved, the content of the organic matters such as dichloropropanol and epoxy chloropropane in the extracted solution of chloride salt is significantly decreased, and the COD value is decreased to less than 4000 ppm. Therefore, no wastewater treatment device is required and the environmental benefits are improved.

(5) The steam consumption is reduced. As described above, in the three stages of high gravity reactors, steam and reaction liquid are in full countercurrent contact, while the oil and water phases are highly crushed and dispersed. The gas-liquid contact heat transfer specific surface area is significantly increased, thus achieving efficient mass and heat transfer between gas and liquid. Moreover, the steam passes through the three stages of reactors in series, and the heat is fully utilized. Therefore, the steam consumption per unit mass of product can be reduced by about half.

(6) The size of the equipment is reduced. The size of the high gravity reactors used in the present application is significantly reduced compared to the traditional tower or tube reactors. Moreover, in the present application, by extracting high-content chloride salt solution through efficient separation, the equipment and place for chloride evaporation and concentration are saved, thus further reducing the occupied area of the device and reducing the investment.

The present application will be described through the following specific examples.

Example 1

A system and a method according to the present application were used for preparing epoxy chloropropane. The used alkali solution was calcium hydroxide solution. The mass fraction (A) of dichloropropanol was 76%. The mass fraction (B) of calcium hydroxide was 20%. The stoichiometric excess value (C) of feed alkali solution relative to dichloropropanol was 5%. The temperature (T1) of the reaction liquid in the first high gravity reactor was 85° C. The high gravity field level (G1) in the first high gravity reactor was 300 g. The high gravity field level (G2) in the second high gravity reactor was 200 g. The high gravity field level (G3) in the third high gravity reactor was 200 g. The mass flow ratio (r) of the circulating liquid fed into the first high gravity reactor for continuous reaction to and the liquid fed into the second high gravity reactor was 7. The vacuum degree (P) of the entire system was 60 KPa. The amount (Q) of water vapor was 300 Kg/(t of epoxy chloropropane). The temperature (T2) of reflux condensate was 8° C. The reaction time (t) was 30 min. The achieved conversion rate ($\alpha$) of dichloropropanol was 98.7%. The purity of epoxy chloropropane ($\beta$) was 98.0%. The concentration ($\gamma$) of calcium chloride in the extracted solution of calcium chloride was 32%. The COD value in the saponification solution was 4000 ppm.

Examples 2-17

The process flow and steps are the same as those in example 1. See Table 1 for the process conditions, operating conditions and corresponding test results of each example. The meanings of the letters and units listed in the header are the same as those in example 1. Due to space limitations, the unit of Q, Kg/(t of epoxy chloropropane), is not listed in the table. The percentages mentioned in all examples are mass percentages.

TABLE 1

Process conditions and test results of examples 2-11

| Example | A | B | C | $T_1$/° C. | $G_1$/g | $G_2$/g | $G_3$/g | r | P/KPa | Q | t/min | $T_2$/° C. | $\alpha$ | $\beta$ | $\gamma$ | COD/ppm |
|---|---|---|---|---|---|---|---|---|---|---|---|---|---|---|---|---|
| 2 | 85 | 20 | 5 | 85 | 300 | 400 | 400 | 7 | 60 | 300 | 30 | 8 | 99.2 | 98.2 | 32 | 4000 |
| 3 | 85 | 15 | 5 | 85 | 300 | 200 | 200 | 7 | 60 | 300 | 30 | 8 | 98.8 | 98.2 | 19 | 5000 |
| 4 | 85 | 20 | 15 | 85 | 300 | 200 | 200 | 7 | 60 | 300 | 30 | 8 | 99.8 | 98.1 | 35 | 3750 |
| 5 | 85 | 20 | 5 | 85 | 300 | 200 | 200 | 7 | 80 | 300 | 30 | 8 | 98.8 | 99.0 | 32 | 2800 |
| 6 | 85 | 20 | 5 | 85 | 800 | 200 | 200 | 7 | 60 | 300 | 30 | 8 | 99.5 | 98.6 | 33 | 2000 |
| 7 | 85 | 20 | 5 | 85 | 30 | 200 | 200 | 7 | 60 | 300 | 30 | 8 | 88.2 | 85.6 | 31 | 12500 |
| 8 | 85 | 20 | 5 | 85 | 30 | 200 | 200 | 7 | 60 | 700 | 30 | 8 | 97.6 | 96.2 | 11 | 9500 |
| 9 | 85 | 20 | 5 | 85 | 300 | 10 | 10 | 7 | 60 | 300 | 30 | 8 | 97.2 | 87.3 | 32 | 10600 |
| 10 | 85 | 20 | 5 | 85 | 300 | 10 | 10 | 7 | 60 | 700 | 30 | 8 | 97.2 | 96.7 | 13 | 9600 |
| 11 | 85 | 20 | 1 | 85 | 300 | 200 | 200 | 7 | 60 | 300 | 30 | 8 | 86.7 | 92.8 | 28 | 13460 |
| 12 | 85 | 20 | 1 | 85 | 300 | 200 | 200 | 7 | 60 | 700 | 30 | 8 | 97.1 | 95.9 | 9 | 8460 |
| 13 | 85 | 20 | 5 | 45 | 300 | 200 | 200 | 7 | 60 | 300 | 30 | 8 | 79.2 | 91.3 | 32 | 17400 |
| 14 | 85 | 20 | 5 | 85 | 300 | 200 | 200 | 2 | 60 | 300 | 30 | 8 | 93.4 | 96.5 | 30 | 9100 |
| 15 | 85 | 20 | 5 | 85 | 300 | 200 | 200 | 7 | 10 | 300 | 30 | 8 | 95.3 | 86.1 | 32 | 12060 |
| 16 | 85 | 20 | 5 | 85 | 300 | 200 | 200 | 7 | 60 | 300 | 30 | 15 | 96.7 | 91.9 | 33 | 11000 |
| 17 | 85 | 20 | 5 | 96 | 300 | 200 | 200 | 7 | 60 | 300 | 30 | 8 | 92.2 | 82.4 | 32 | 15300 |

Among all examples, the process parameters of examples 1-6 are within the process parameter ranges claimed by the present application. From the results of the examples, it can be concluded that the present application can significantly improve the conversion rate of raw materials and the purity of products, and solve the problems such as equipment blockage and high steam consumption in the traditional methods. At the same time, the present application can significantly improve the salt concentration in the chloride salt solution and reduce the content of the organic matters therein.

Among all examples, partial process and operating parameters of examples 7-17 are out of the process parameter ranges claimed by the present application, which are comparative examples. As can be proven in reverse by the comparative examples, the process parameters claimed in this aspect can simultaneously achieve several process indicators such as high conversion rate, high product purity, low steam consumption, high-concentration chloride salt extraction with low content of organic matters; in case of deviating from the process and operating parameter ranges claimed in the present application, one or more of the above process indicators will not be achieved.

From the detailed description of the technical solution above, it can be seen that, in the present application, by coupling three stages of high gravity reactors, the product epoxy chloropropane and water vapor are distilled from a reaction system in form of an azeotrope by adopting a water vapor steam stripping method, and the product obtained using the method has high purity. On the one hand, water vapor is replenished through an external water vapor source, and on the other hand, it can be recycled from the second high gravity reactor and the third high gravity reactor to form a water vapor cycle, thus ensuring the amount of water vapor used and not requiring a large amount of water vapor. Further, the combination of the azeotrope with the multiple stages of high gravity reactors greatly improves the gas-phase and liquid-phase mass transfer effect of the azeotrope aiming at the features of the azeotrope in the reaction system of the present application, thus improving the overall conversion rate of the reaction. In addition, by combining steam stripping and high gravity, dichloropropanol and alkali solution are rapidly mixed for mass transfer, and the product epoxy chloropropane is rapidly distilled from the reaction system in form of the azeotrope (based on rapid diffusion of water vapor), such that the reaction proceeds continuously towards the direction of producing epoxy chloropropane, thus significantly improving the conversion rate. As proved by a test apparatus, the present application can make the conversion rate of dichloropropanol reach 99.6% or more and make the purity of the product epoxy chloropropane reach 99% or more.

The various examples in the description are described in a progressive manner. For the same and similar parts in the examples, mutual reference may be made. Each example focuses on the difference from other examples. Especially for the system example, due to its basic similarity to the method example, the description is relatively simple. For relevant details, please refer to the description of the method example.

In the description, the reference terms "an implementation", "some implementations", "examples", "specific examples", or "some examples" refer to that the specific features, structures, materials, or characteristics described in combination with the implementation or example are included in at least one implementation or example in the description. The schematic expressions of the above terms in the description do not necessarily refer to the same implementation or example.

In addition, those skilled in the art may combine different implementations or examples described in the description and the features of different implementations or examples without causing mutual contradiction. The above description only describes the examples of the present application and is not intended to limit the examples of the present application. Those skilled in the art may make various changes and variations to the examples of the present application. Any modifications, equivalent replacements, improvements and the like made within the spirit and principle of the present application shall be included within the scope of the claims of the present application.

The invention claimed is:

1. A system for preparing epoxy chloropropane, comprising:
   a first high gravity reactor, a liquid inlet of the first high gravity reactor being communicated with a liquid inlet pipeline of raw materials dichloropropanol and alkali solution;
   a second high gravity reactor, a gas inlet of the second high gravity reactor being communicated with a water vapor pipeline, a gas outlet of the second high gravity reactor being communicated with a gas inlet of the first high gravity reactor;
   a liquid circulation tank, an inlet of the liquid circulation tank being communicated with a liquid outlet of the first high gravity reactor, an outlet of the liquid circulation tank being respectively communicated with the liquid inlet of the first high gravity reactor and a liquid inlet of the second high gravity reactor; and
   a third high gravity reactor, a gas inlet of the third high gravity being communicated with a gas outlet of the first high gravity reactor, a liquid outlet of the third high gravity being communicated with the liquid inlets of the first high gravity reactor and the second high gravity reactor, a gas outlet of the third high gravity reactor being communicated with a recovery device, a liquid inlet of the third high gravity reactor being communicated with a liquid outlet of the recovery device, wherein
   a liquid outlet of the second high gravity reactor is communicated with an inlet of a chloride salt solution storage tank.

2. The system according to claim 1, wherein the system further comprises:
   a first valve located on a pipeline between the outlet of the liquid circulation tank and the liquid inlet of the first high gravity reactor; and
   a second valve located on a pipeline between the outlet of the liquid circulation tank and the liquid inlet of the second high gravity reactor.

3. The system according to claim 2, wherein the system further comprises:
   a valve controller coupled with at least one of the first valve or the second valve and configured to control the opening of the at least one of the first valve or the second valve.

4. The system according to claim 3, wherein the system further comprises:
   a detector configured to detect flow rate at the liquid inlet pipeline of raw materials dichloropropanol and alkali solution; and
   a processor configured to determine the opening of the at least one of the first valve or the second valve according to the flow rate.

5. The system according to claim 1, wherein the recovery device comprises:
   a first condenser and a second condenser in series, a gas inlet of the first condenser being communicated with a gas outlet of the third high gravity reactor; and
   a two-phase separator communicated with liquid outlets of the first condenser and the second condenser, a liquid outlet of the two-phase separator being communicated with the liquid inlet of the third high gravity reactor.

6. The system according to claim 1, wherein the second high gravity reactor and the third high gravity reactor are rotating packed beds, and the first high gravity reactor is a rotor-stator reactor.

7. The system according to claim 5, wherein the two-phase separator comprises a separation chamber and a baffle provided in the separation chamber, the baffle divides the separation chamber into two communicated sub-chambers, one sub-chamber is communicated with the third high gravity reactor, and the other sub-chamber is communicated with a storage tank.

8. The system according to claim 7, wherein the baffle is movable.

9. The system according to claim 1, wherein the second high gravity reactor and the third high gravity reactor are rotating packed beds, and an oleophobic packing is provided in the rotating packed beds.

10. A method for preparing epoxy chloropropane, comprising:

preparing epoxy chloropropane by using the system according to claim 1.

* * * * *